United States Patent [19]

Kieran et al.

[11] Patent Number: 4,607,050
[45] Date of Patent: Aug. 19, 1986

[54] METHOD OF CONTROLLING INSECTS AND PARASITES WITH AN AQUEOUS LOCALIZED POUR-ON FORMULATION

[75] Inventors: Peter J. Kieran, Beecroft; Robert B. Townsend, Waitara; Ronald J. Hackney, Croydon Park; Stephen Gayst, Double Bay; Michael J. Maguire, North Epping, all of Australia

[73] Assignee: Wellcome Australia Limited, Cabarita, Australia

[21] Appl. No.: 430,884

[22] Filed: Sep. 30, 1982

[30] Foreign Application Priority Data

Oct. 19, 1981 [AU] Australia ............................... PF1217

[51] Int. Cl.⁴ .................. A61K 31/275; A61K 31/215
[52] U.S. Cl. ...................................... 514/520; 514/531
[58] Field of Search .................. 424/7.1, 270, 304; 514/531, 520

[56] References Cited

U.S. PATENT DOCUMENTS

| | | | |
|---|---|---|---|
| 2,496,270 | 2/1950 | Coler | 424/7.1 |
| 2,751,383 | 6/1956 | Trosken | 424/7.1 |
| 3,980,791 | 9/1976 | Schulz et al. | 424/270 |
| 4,018,932 | 4/1977 | Spicer et al. | 424/270 |
| 4,070,476 | 1/1978 | Brooker et al. | 424/304 |
| 4,325,969 | 4/1982 | Brown | 424/304 |
| 4,341,760 | 7/1982 | Matthewson | 424/304 |
| 4,479,968 | 10/1984 | Hyman et al. | 424/330 |

FOREIGN PATENT DOCUMENTS

| | | |
|---|---|---|
| 6459780 | 5/1981 | Australia . |
| 1218583 | 9/1983 | Australia . |
| 1591106 | 6/1981 | United Kingdom . |
| 1591105 | 6/1981 | United Kingdom . |

OTHER PUBLICATIONS

Clout Technical Bulletin–Wellcome Australia Limited.
Clout "S" Technical Bulletin–Wellcome Australia Limited.

Primary Examiner—Sam Rosen
Attorney, Agent, or Firm—Donald Brown

[57] ABSTRACT

An aqueous pour-on formulation for localized external application to animals comprises an aqueous carrier, an effective amount of a water-insoluble anti-parasitic agent suspended or dispersed in the aqueous carrier, and a colored dye to enable the application to be observed. Preferred water-insoluble agents include pyrethroids, organophosphorus compounds, formamidines, thiazoles and avermectins. Use of an aqueous system avoids skin reactions sometimes found when non-aqueous solvent systems are used.

11 Claims, No Drawings

METHOD OF CONTROLLING INSECTS AND PARASITES WITH AN AQUEOUS LOCALIZED POUR-ON FORMULATION

The present invention relates to a pour-on formulation which is water based, and to a method of treating animals.

In the past, animals have generally been treated for the control of insects, and internal and external parasites, by either dipping the whole animal in a bath containing the parasitically effective agent or by spraying the entire body surface. More recently, it has been found that a number of parasitically effective substances may be applied by a localised (so-called "pour-on") application—but yet the active agent migrates so as to protect the whole external surface of the animal. By "localised application" is meant that the active agent is only applied to a minor portion of the outer surface of the animal, generally as a line or spot on the animal's back. However, not all active agents are suitable since not all show the potential for migration.

Hitherto, the active agent, particularly a pyrethroid or organophosphorus compound, has been dissolved in a non-aqueous solvent system to produce a suitable pour-on formulation. In general, the pyrethroids and other active agents of interest are only soluble in non-aqueous systems, and the need to dissolve the active agent in the pour-on formulation has therefore limited pour-on formulations to non-aqueous systems.

However, it is becoming apparent that non-aqueous systems possess a number of disadvantages. Thus, it has been found that the use of solvent-based pour-on formulations can cause irritation of the skin of treated sheep, depending on the solvents used. There may also be handling problems resulting from the flammability or toxicity of the solvents.

Contrary to previous belief, it has now been surprisingly found that it is not necessary to dissolve the active agent in the pour-on formulation in order that the formulation be insecticidally or parasitically effective. This discovery has enabled the production of aqueous pour-on formulations wherein the active agent is present in the dispersed or suspended form. Such aqueous formulations have a wide variety of advantages including convenience, reduced toxicity, reduced skin irritation, and increased environmental acceptability.

Aqueous suspensions of insecticides and parasiticides are not new in themselves (see published Australian patent applications Nos. 40079/78, 40080/78 and 32016/77); nor are emulsifiable concentrates or emulsions intended for dilution with water to make up a dip bath. However, it was previously unknown to use such aqueous formulations for localised external application since it was believed that dissolution of the parasiticide was necessary in order for the parasiticide to migrate over the external surface of the animal (or in order to become systemically absorbed).

Thus, one aspect of the present invention provides an aqueous pour-on formulation for localised external application to animals which comprises an aqueous carrier, an effective amount of a water-insoluble insecticidal or anti-parasitic agent suspended or dispersed in the aqueous carrier, and a colouring agent.

Formulations intended for pour-on application (which term includes localised application by spraying) almost invariably include a colouring agent to enable the farmer or grazier to visually monitor the application of the formulation to the animal. This is not true of formulations for parenteral use or for use in making up dip baths.

The nature of the colouring agent is unimportant and a wide variety of suitable dyes and pigments will be known to the skilled man. The colouring agent may be soluble or insoluble in water.

The anti-parasitic agent is insoluble in water. By this is meant that the water-solubility is insufficient for an effective amount of the agent to be dissolved in a normal pour-on dose of the formulation (generally in the region 2-15 ml).

When the active agent is a solid, for example the pyrethroid decamethrin (also called deltamethrin), the agent will be suspended in the aqueous carrier. In order for a satisfactory suspension to be produced and for the active agent to exert a good anti-parasitic effect, it is desirable that the solid agent have a particle size of less than 10 microns, preferably in the range 2-5 microns.

When the active agent is a liquid, for example the organophosphorus fenitrothion, it will be present as a dispersion; usually an oil-in-water emulsion.

Generally, the formulation will contain a suitable suspending agent. The suspending agent may be selected from cellulose derivatives (e.g. AVICEL microcrystalline cellulose, anionic or non-ionic cellulose ethers), vegetable gums such as xantham gums, fumed silica, colloidal silicon dioxide, alginates, polyvinylpyrrolidone polymers, magnesium aluminium silicates such as VEEGUM, and mixtures of these.

If suitable application techniques (e.g. high pressure jetting) are used a wetting agent may not be necessary. However, in general it is preferred to include a wetting agent capable of lowering the surface tension of the formulation to 20-30 dynes/cm. Suitable wetting agents include polyoxyethylene sorbitan esters, polyoxyethylene fatty alcohol ethers, sorbitan esters, ethoxylated propoxylated block copolymers, polyethylene glycol fatty acid esters, sulphated fatty alcohols, nonyl phenol ethoxylates, quaternary ammonium compounds, and alkyl naphthalene sulphonates.

Particularly good results are found with polyalkylene oxide modified dimethylpolysiloxanes, such as SILWET (Trade Mark of Union Carbide); and with fluoroaliphatic polymeric esters, such as FLUORAD (Trade Mark of the 3M Company). Both of these wetting agents show enhanced wetting and spreading properties when applied to sheep.

The formulation may also be formulated for application by a spray technique, e.g. as an aerosol including a liquid or gaseous propellant.

Depending on the efficacy of the particular active agent used, the formulation will generally contain from 0.1 to 500 g/liter, preferably 1 to 250 g/liter, of the active agent.

The active agent is active against insects and/or parasites, including lice, ticks, keds, mites and flies. Generally, the pour-on formulation will be used to control external parasites. However, where dermal penetration may be achieved, the formulation may also exert a systemic effect in the control of internal parasites.

Water-insoluble active agents particularly suitable in the present invention include pyrethrins, pyrethroids, water-insoluble organophosphorus compounds, formamidines, water-insoluble thiazoles, avermectins (or milbemycins) and mixtures thereof. Suitable milbemycins are disclosed in Australian published patent applications numbers 42309/79 and 42389/78.

Preferred pyrethroids have the formula

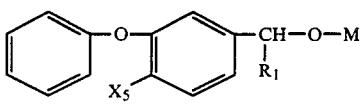
(I)

wherein
M is

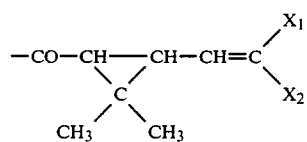

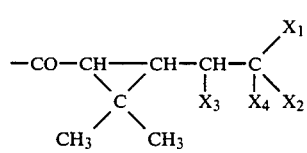

or

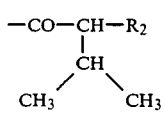

and wherein

X$_1$ to X$_4$ are independently selected from halo C$_1$–C$_4$ alkyl, halogen-substituted C$_1$–C$_4$ alkyl, and halogen-substituted phenyl;

X$_5$ is —H or halo;

R$_1$ is —H or cyano; and

R$_2$ is halogen-substituted phenyl.

Particularly preferred compounds are presented in Tables I to III.

TABLE I

M = —CO—CH——CH—CH=C(X$_1$)(X$_2$) with C(CH$_3$)(CH$_3$)

| No. | X$_1$ | X$_2$ | X$_3$ | X$_4$ | X$_5$ | R$_1$ | trivial name |
|---|---|---|---|---|---|---|---|
| 1 | Cl | Cl | — | — | H | H | permethrin |
| 2 | CH$_3$ | CH$_3$ | — | — | H | H | phenothrin |
| 3 | Br | Br | — | — | H | CN | decamethrin |
| 4 | Cl | Cl | — | — | H | CN | cypermethrin |
| 5 | Cl | CF$_3$ | — | — | H | CN | cyhalothrin |
| 6 | Cl | —⟨⟩—Cl | — | — | F | CN | flumethrin |
| 7 | Cl | Cl | — | — | F | CN | cyfluthrin |
| 8 | CH$_3$ | CH$_3$ | — | — | H | CN | cyphenothrin |

TABLE II

M = —CO—CH——CH—CH—C(X$_1$)(X$_3$)(X$_4$)(X$_2$) with C(CH$_3$)(CH$_3$)

| No. | X$_1$ | X$_2$ | X$_3$ | X$_4$ | X$_5$ | R$_1$ | trivial name |
|---|---|---|---|---|---|---|---|
| 9 | Br | Br | Br | Br | H | CN | tralomethrin |
| 10 | Cl | Cl | Br | Br | H | CN | tralocythrin |

TABLE III

M = —CO—CH—R$_2$ with CH(CH$_3$)(CH$_3$)

| No. | R$_2$ | X$_5$ | R$_1$ | trivial name |
|---|---|---|---|---|
| 11 | —⟨⟩—Cl | H | CN | fenvalerate |

Preferred water-insoluble organophosphorus compounds which may form stable aqueous suspensions or dispersions include the following:

O,O-diethyl-O-(3-chloro-4-methyl-7-coumarinyl)phosphorothioate (coumaphos);

O,O-diethyl-O-(2-isopropyl-6-methyl-pyrimidin-4-yl)phosphorothioate (diazinon);

2,3-p-dioxanedithiol S,S-bis, O,O-diethyl phosphorodithioate (dioxathion);

O-ethyl-O-(quinol-8-yl)phenylphosphorothioate (oxinothiophos);

(S-{5,7-dichlorobenzoxazol-2-yl-methyl}-O,O-diethylphosphorodithioate) (benoxaphos);

O,O-dimethyl-O-2,4,5-trichlorophenyl phosphorothioate (fenchlorphos);

O,O-dimethyl-O-(4-dimethylsulfamoylphenyl)phosphorothioate (famphur);

O,O-dimethyl-O-(4-nitro-m-tolyl)phosphorothioate (fenitrothion); and

S-[5-dimethyl-2-oxo-2,3-dihydro-1,3,4-thiadiazol-3-yl]methyl dimethyl phosphorothio/othionate (methidathion).

Preferred formamidines include water-insoluble compounds of the formula

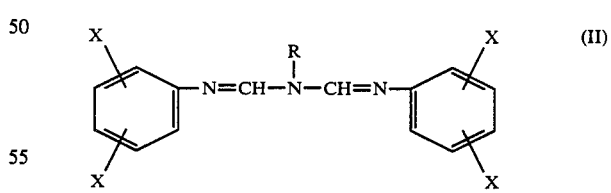
(II)

wherein R is hydrogen or C$_1$–C$_6$ alkyl, and each X is independently selected from hydrogen, C$_1$–C$_6$ alkyl and halo.

Particularly preferred formamidines include N,N-di-(2,4-xylyliminomethyl)-methylamine (called amitraz). Amitraz has very limited solubility in water and may hydrolyse slowly. It is preferred to encapsulate the amitraz particles according to known techniques to avoid hydrolysis.

Preferred thiazoles include water-insoluble compounds of the formula $$\text{Ar} \diagdown \underset{\underset{N}{|}}{\overset{N}{\diagup}} \diagdown \overset{S}{\diagup} \quad (III)$$

wherein Ar is selected from phenyl, benzyl, and naphthyl, optionally substituted with a $C_1$–$C_5$ alkyl, halo or nitro group, provided that the dotted line indicates a bond which is optionally present.

The mixture of isomers wherein Ar is phenyl is water-insoluble and is named tetramizole. Levamisole and dexamisole are preferred isomers.

The use of water-based formulations also helps alleviate formulation problems when two or more active agents are to be included, for example when one agent is water-soluble and the other is water-insoluble. For instance, it may be desirable to formulate a water-insoluble pesticidal pyrethroid with a water-soluble anthelmintic thiazole (e.g. levamisole hydrochloride) in order to provide a formulation having a chosen spectrum of activity. Such formulations are difficult to devise when it is necessary to find a solvent system suitable for dissolving both active agents.

Water-based formulations may also be used where two incompatible active agents are to be included, e.g. amitraz and deltamethrin; and levamisole and deltamethrin mixtures. In this case one or both agents may be encapsulated or provided in homogenous wax beadlets to avoid contact with each other during storage. In this way each active agent may have its optimum close environment as regards pH, stabilisers etc. Surprisingly, encapsulation or beadlet formation has not been found to hinder the action of the active agents when applied as an aqueous pour-on.

If desired, the various constituents of the formulation may be separately provided within a common package. For example, the package might contain an aqueous suspension of a pyrethroid in one part together with a wettable formamidine powder as a second part; the two parts being mixed up to 24 hours prior to use to avoid hydrolysis of the thiazole.

The invention in a second aspect provides a method of controlling parasites which comprises making a localised external application of the aqueous pour-on formulation to an animal (but excluding the application of a pyrethroid-containing formulation to sheep).

The animal is preferably a mammal, and may be selected from cattle, goats, pigs, horses, deer and sheep. The animal may also be a bird, e.g. selected from ducks, chickens and geese.

Generally, the pour-on formulation is applied by pouring a line or spot on the back of the animal. Alternatively, it may be applied by means of a localised spray.

It is a particular advantage of the use of pour-on formulations that only small volumes of the formulation need to be applied. Depending on the size of the animal, the volume applied will generally lie in the range 2–15 ml.

Preferred formulations will now be described by way of example only as follows. In each formulation the colouring agent is a suspension of Fast Scarlet Pigment 3610 (obtained from BSAF).

EXAMPLE 1

An aqueous suspension of the pyrethroid decamethrin (also called deltamethrin) as active agent was prepared by suspending micronised technical decamethrin of average particle size 2 to 5 microns to produce an aqueous formulation containing:

| | |
|---|---|
| micronised decamethrin | 10.1 g |
| non-ionic wetting agent | 1.5 g |
| (1 mole nonylphenol condensed with 15 moles of ethylene oxide) | |
| fumed silicon dioxide (anti-settling agent) | 5.0 g |
| xantham gum (viscoliser) | 4.0 g |
| propylene glycol (anti-freeze) | 60.0 g |
| formaldehyde (preservative) | 1.0 g |
| silicone oil (antifoaming agent) | 0.1 g |
| water (and pigment) | to one liter. |

Various other decamethrin suspensions in the range 1 to 500 g/l decamethrin were also prepared.

EXAMPLE 2

An aqueous suspension of decamethrin using Silwet (Trade Mark) surfactant was prepared as follows:

| | |
|---|---|
| micronised decamethrin | 10.1 g |
| Silwet L-77 | 10.0 g |
| fumed silicon dioxide | 5.0 g |
| xantham gum | 4.0 g |
| propylene glycol | 60.0 g |
| formaldehyde | 1.0 g |
| silicon oil | 0.1 g |
| water (and pigment) | to one liter. |

Various other suspensions were also prepared containing concentrations of decamethrin in the range 1 to 500 g/l.

EXAMPLE 3

An aqueous suspension of decamethrin using Fluorad (Trade Mark) surfactant was prepared as follows:

| | |
|---|---|
| micronised decamethrin | 10.1 g |
| Fluorad FC 430 | 5.0 g |
| fumed silicon dioxide | 5.0 g |
| xantham gum | 4.0 g |
| propylene glycol | 60.0 g |
| formaldehyde | 1.0 g |
| silicon oil | 0.1 g |
| water (and pigment) | to one liter. |

EXAMPLE 4

An aqueous formulation was prepared as in Example 2 but containing as active ingredient the organophosphorus compound fenitrothion in an amount of 100 g/l as an emulsified oil.

EXAMPLE 5

An aqueous formulation was prepared as in Example 1 but containing as active ingredient the formamidine amitraz in an amount of 250 g/l. The amitraz particles were encapsulated according to known techniques to prevent hydrolysis by the aqueous carrier.

EXAMPLE 6

An aqueous formulation was prepared as in Example 2 but containing as active ingredients 10 g/l micronised decamethrin and 100 g/l fenitrothion (present as an emulsified oil).

EXAMPLE 7

An aqueous formulation was prepared as in Example 2 but containing as active ingredients 10 g/l micronised decamethrin and 200 g/l water-soluble thiazole levamisole hydrochloride (anthelmintic). If necessary the concentration of wetting agent may be varied to optimise wetting of the particular animal being treated, thereby maximising dermal absorption of the levamisole hydrochloride.

EXAMPLE 8

An aqueous formulation was made up as in Example 2 but containing as active ingredients 10 g/l micronised decamethrin and 250 g/l of the formamidine amitraz. The amitraz was encapsulated to prevent hydrolysis.

EXAMPLE 9

An aqueous formulation was prepared as in Example 2 but containing as active ingredients 100 g/l water-insoluble particulate organophosphorus compound fenchlorphos and 100 g/l water-soluble thiazole levamisole hydrochloride (anthelmintic).

EXPERIMENTAL TESTS (SHEEP)

A series of trials were carried out to demonstrate the efficacy of the aqueous formulations in the control of the sheep biting louse (*Damalinia Ovis*) on merino sheep. Localised applications (i.e. as a line or spot on the sheep's back) were made within 24 hours of shearing. Lice counts were taken at the time of shearing and after 4, 6 and 8 weeks. The active agent was decamethrin at 10 g/l or 25 g/l in a formulation according to Example 1 or 2.

Test 1

The result of lice counts are given in Table 1. The degree of control is good and quite comparable to that attained using the same concentrations of decamethrin dissolved in non-aqueous solvent systems (see our published Australian patent application No. 77004/81).

TABLE 1

| Treatment | Sheep Number | Weight (kg) | Dose (ml) | # pre-treatment | week 4 | week 6 | week 8 |
|---|---|---|---|---|---|---|---|
| Suspension 10 g/l deltamethrin | 160 | 27 | 6 | light-medium* | 0 | 0 | 0 |
| | 206 | 34 | 8 | light | 0 | 0 | 0 |
| | 247 | 38 | 8 | light | 0 | 0 | 0 |
| Suspension 25 g/l deltamethrin (low volume "spot-on" treatment) | 179 | 37 | 4 | medium* | dead | — | — |
| | 196 | 32 | 4 | very light | 6 | 0 | 0 |
| | 474 | 45 | 5 | light | 0 | 0 | 0 | prior to shearing
*after shearing

Test 2

Trials were carried out to determine whether or not wetting of the sheep (to simulate heavy rainfall) had any effect on the efficacy of the aqueous formulations on the control of lice.

Sheep were wetted prior to, 1, 5 and 14 days after treatment with a suspension containing 10 g/l decamethrin.

The results in Table 2 show good control and surprisingly indicate that wetting has no effect.

TABLE 2

| Group no. | Treatment | Sheep no. | Weight (kg) | Dose (ml) | Louse Count* Week 3 | Louse Count Week 5 |
|---|---|---|---|---|---|---|
| 1 | Wet immediately to treatment | 609 | 27 | 6 | 0 | 0 |
| | | 613 | 28 | 6 | 0 | 0 |
| | | 619 | 31 | 8 | 0 | 0 |
| | | 622 | 25 | 6 | 0 | 0 |
| | | 630 | 27 | 6 | 0 | 0 |
| 2 | Wet 1 day after treatment | 611 | 28 | 6 | 0 | 0 |
| | | 617 | 30 | 6 | 0 | 0 |
| | | 623 | 28.5 | 6 | 0 | 0 |
| | | 629 | 27.5 | 6 | 0 | 0 |
| | | 631 | 25.5 | 6 | 0 | 0 |
| 3 | Wet 5 days after treatment | 608 | 28.5 | 6 | 0 | 0 |
| | | 610 | 32 | 8 | 0 | 0 |
| | | 612 | 21 | 6 | 0 | 0 |
| | | 615 | 34 | 8 | 0 | 0 |
| | | 624 | 31.5 | 8 | 0 | 0 |
| 4 | Wet 14 days after treatment | 605 | 25.5 | 6 | 0 | 0 |
| | | 607 | 28.5 | 6 | 0 | 0 |
| | | 616 | 23 | 6 | <1/20# | 0 |
| | | 625 | 30.5 | 8 | 0 | 0 |
| | | 627 | 23.5 | 6 | 0 | 0 |
| 5 | Untreated non-wet control group | 606 | 27 | 0 | 5 | +ve |
| | | 618 | 23 | 0 | 61 | +ve |
| | | 621 | 28.5 | 0 | 36 | +ve |
| | | 626 | 26 | 0 | 95 | +ve |

*Numbers against control sheep denote the number of lice per 20 wool partings and numbers against treated sheep denote the number of lice in more than 50 wool partings.
1 immature

EXPERIMENTAL TESTS (GOATS)

A range of lice-infested Angora goats—does of various ages having liveweights ranging from 15 kg to 35 kg and young kids—were treated with an aqueous pour-on suspension of decamethrin at a concentration of 10 g/l. The does were shorn prior to treatment and the kids were not shorn. The does were weighed and treated at a dosage rate of 2 ml 10 g/l deltamethrin aqueous suspension per 10 kg liveweight. The unshorn kids were treated at approximately 2× this standard dosage rate. The goats were inspected pre-treatment and six weeks post-treatment.

Five sites alone one side of the body were examined after shearing, viz. neck, shoulder, wither, flank and rump. Infestation was scored for each area:
Very light = 1
Light = 2
Moderate = 4
Heavy = 6
Total possible 5 (areas) × 6 ("heavy") = 30

All goats were infested with the biting louse, tentatively identified as *Damalinia caprae*, and there were also a few sucking lice present (*Linognathus stenopsis*).

The results given in Table 3 show that the lice were completely eradicated.

TABLE 3

| Goat No. | Pre-treatment "Score" | Post-treatment "Score" |
|---|---|---|
| (shorn) | | |
| 2 | 4 | 0 |
| 6 | 4 | 0 |
| 6+ | 30 | 0 |
| 10 | 11 | 0 |

TABLE 3-continued

| Goat No. | Pre-treatment "Score" | Post-treatment "Score" |
|---|---|---|
| 11 | 5 | 0 |
| 13 | 5 | 0 |
| 16 | 2 | 0 |
| 21 | 4 | 0 |
| 32 | 5 | 0 |
| 265 | 20 | 0 |
| G 3 | 30 | 0 |
| 5 | 13 | 0 |
| O 9 | 5 | 0 |
| B 36 | 14 | 0 |
| (unshorn) | | |
| 18 | | 0 |
| 27 | | 0 |
| 29 | | 0 |
| 34 | | 0 |
| 35 | | 0 |
| 44 | | 0 |
| 45 | | 0 |
| 580/45 | | 0 |

EXPERIMENTAL TESTS (CATTLE)

Hereford calves (age 10 months) of liveweights ranging from 195 to 238 kg and bearing infestations of *Damalinia bovis* (Db), *Haematopinus eurysternus* (He), *Linognathus vituli* (Lv) and *Solenopotes capillatus* (Sc) were treated with an aqueous pour-on suspension of decamethrin at a concentration of 20 g/l.

The lice scores for the whole animal body were recorded prior to treatment, and 1, 2, 3, 4 and 5 weeks after treatment.

The results given in Table 4 show that three species of lice were completely eradicated. Only very low numbers of the fourth louse species, *Solenopotes capillatus*, persisted after five weeks on two cattle.

TABLE 4

| Beast | Pre-treatment Lice Scores | | | | Post-treatment Scores (Weeks) | | | | |
|---|---|---|---|---|---|---|---|---|---|
| | Db | He | Lv | Sc | 1 | 2 | 3 | 4 | 5 |
| 1 | 33 | — | — | 19 | 1(Sc) | 1(Sc) | 2(Sc) | 2(Sc) | 3(Sc) |
| 2 | 30 | 26 | 22 | 26 | 5(Sc) | 5(Sc) | 3(Sc) | 3(Sc) | 1(Sc) |
| 3 | 28 | — | 1 | 5 | 0 | 0 | 0 | 0 | 0 |
| 4 | 31 | 1 | — | 20 | 2(Sc) | 1(Sc) | 0 | 0 | 0 |
| 5 | 57 | — | — | 1 | 1(Sc) | 1(Sc) | 1(Sc) 1(Sc) | 0 | |

The claims defining the invention are as follows:

1. A method of controlling insects or parasites which comprises making a localized external pour-on application of a small volume of an aqueous pour-on formulation to a minor portion of the outer surface of a mammal; said aqueous pour-on formulation comprising
   (a) an aqueous carrier;
   (b) an effective amount of a nondissolved water-insoluble insecticidal or antiparasitic agent suspended or dispersed in the aqueous carrier; and
   (c) wherein said water insoluble agent is a pyrethrin or a pyrethroid of the formula

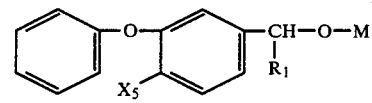

wherein
M is

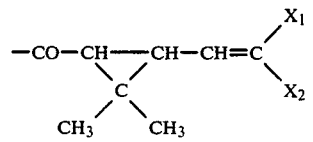

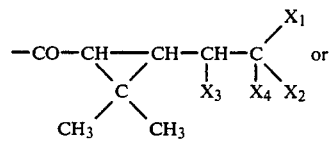

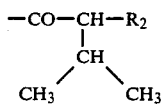

wherein
$X_1$ to $X_4$ are independently selected from halo, $C_1$-$C_4$ alkyl, halogen-substituted $C_1$-$C_4$ alkyl, and halogen-substituted phenyl,
$X_5$ is H or halo,
$R_1$ is H or cyano, and
$R_2$ is halogen-substituted phenyl.

2. The method of claim 1 in which the formulation is applied by means of a localized spray.

3. The method of claim 1 in which the formulation is applied to the back of the mammal.

4. A method according to claim 1 wherein 2 to 15 ml of the formulation is applied.

5. A method according to claim 2 wherein 2 to 15 ml of the formulation is applied.

6. A method according to claim 3 wherein 2 to 15 ml of the formulation is applied.

7. A method according to claim 1 in which the aqueous carrier has a coloring agent therein.

8. A method for control of insects or parasites of an animal consisting essentially of the topical application to a localized area of the animal body surface of a pour-on formulation consisting essentially of an aqueous carrier; micronized decamethrin, permethrin or cypermethrin suspended or dispersed in said aqueous carrier and a wetting agent in an amount sufficient to lower the surface tension of the formulation to 20 to 30 dynes/cm.

9. The method of claim 8 in which the animal is a sheep.

10. The method of claim 8 which comprises micronized permethrin in said aqueous carrier.

11. The method of claim 10 in which the animal is a sheep.

* * * * *